US009291573B2

(12) United States Patent
Baych et al.

(10) Patent No.: US 9,291,573 B2
(45) Date of Patent: Mar. 22, 2016

(54) LASER INSPECTION SYSTEM AND METHODS

(71) Applicant: PFM Integrators Inc., Chaska, MN (US)

(72) Inventors: Ken Baych, Chaska, MN (US); Danney Winkelman, Chaska, MN (US)

(73) Assignee: PFM INTEGRATORS INC., Chaska, MN (US)

( * ) Notice: Subject to any disclaimer, the term of this patent is extended or adjusted under 35 U.S.C. 154(b) by 172 days.

(21) Appl. No.: 14/095,687

(22) Filed: Dec. 3, 2013

(65) Prior Publication Data

US 2015/0153288 A1    Jun. 4, 2015

(51) Int. Cl.
| | | |
|---|---|---|
| G01B 11/28 | (2006.01) | |
| G01B 5/00 | (2006.01) | |
| G01B 11/00 | (2006.01) | |
| B65B 43/00 | (2006.01) | |
| G01N 21/90 | (2006.01) | |
| G01B 11/06 | (2006.01) | |
| G01B 5/06 | (2006.01) | |
| G01B 5/02 | (2006.01) | |

(52) U.S. Cl.
CPC .............. *G01N 21/9054* (2013.01); *G01B 5/02* (2013.01); *G01B 5/06* (2013.01); *G01B 11/0691* (2013.01)

(58) Field of Classification Search
CPC .. G01N 21/9054; G01B 11/0691; G01B 5/02; G01B 5/06
USPC ................... 33/783, 784, 791, 792; 356/630; 53/313, 329, 329.4, 373.7, 374.8, 561, 53/570; 29/889.1, 402.04, 402.09, 430, 29/564.1
See application file for complete search history.

(56) References Cited

U.S. PATENT DOCUMENTS

| | | | | | |
|---|---|---|---|---|---|
| 4,110,148 | A | * | 8/1978 | Rocholl | E06B 3/67339 156/109 |
| 5,210,593 | A | * | 5/1993 | Kramer | G01B 11/0691 250/559.27 |
| 6,281,679 | B1 | * | 8/2001 | King | G01B 7/107 324/226 |
| 7,206,076 | B2 | * | 4/2007 | Blalock | G01B 11/0691 356/479 |
| 8,654,353 | B2 | * | 2/2014 | Kuo | G01B 11/0691 356/602 |
| 2004/0090639 | A1 | * | 5/2004 | Kubo | G01B 21/30 356/630 |
| 2005/0157314 | A1 | * | 7/2005 | Typpoe | D21F 7/06 356/630 |
| 2006/0181715 | A1 | * | 8/2006 | Bristow | G01B 11/06 356/630 |
| 2009/0142082 | A1 | * | 6/2009 | Ferran | B41J 11/009 399/45 |
| 2011/0237150 | A1 | * | 9/2011 | Ito | C03C 23/0025 445/44 |

OTHER PUBLICATIONS

5KEYENCE High-speed 2D/3D Laser Scanner LJ-V7000 Series. Keyence Corporation 2013, 25 pages.

* cited by examiner

*Primary Examiner* — Tarifur Chowdhury
*Assistant Examiner* — Sunghee Y Gray
(74) *Attorney, Agent, or Firm* — Fredrikson & Byron, P.A.

(57) ABSTRACT

Systems and methods for inspecting the integrity of a sealed package are described. A system can include an inspection station and a control unit. The inspection station can include a scanning platform, a first scanner, and a second scanner. The first scanner can measure a first distance from the first scanner to the seal and the second scanner can measure a second distance from second scanner to the seal. The control unit can move the package to a first station or a second station based on the difference between a gap distance and combined first distance and second distance. A method of inspecting the integrity of a seal using any of the embodiments of the inspection system are described.

20 Claims, 4 Drawing Sheets

LASER INSPECTION SYSTEM AND METHODS

TECHNICAL FIELD

This disclosure generally relates to systems and methods for inspecting the integrity of a sealed package.

BACKGROUND

Re-sealable packages are often used in the food packaging industry to store packaged food products (e.g.: chips, beef jerky). Food packaging often involves the steps of drying and adding preservatives to the food product, placing the food product in a plastic package, flushing the package with nitrogen or a similar inert gas to remove moisture, and vacuum sealing the package to remove oxygen and any other trapped gases. These steps can be completed in an automated process as a part of a food packaging production line. Such vacuum-sealed packages can typically have a re-sealable seam or oxygen and moisture absorbers (e.g.: silica gel packets) to maintain a hermetic seal after a permanent seal is broken to gain access to the contents of the package.

A predetermined threshold for moisture and oxygen often exists to maintain freshness of the packaged food, and if these thresholds are exceeded, pathogenic growth (e.g. aerobic bacteria, fungi etc.) can occur in the packaged food product, leading to food spoilage or diminished shelf-life of food products. It is often the case that an article of the food product can get trapped in the permanent seal during the automated process of vacuum sealing the package, which may lead to a poor seal and, the possibility of food spoilage. An exemplary system and method to inspect the integrity of a sealed package can include randomized visual inspection of the package by a user. Such systems, however, do not offer a fast and accurate assessment of the integrity of the seal.

SUMMARY

One embodiment includes a system for determining integrity of a package with a seal wherein an integral seal has a predetermined thickness. The system includes an inspection station operatively coupled to a transport module and a control unit operatively coupled to the inspection station. The inspection station includes a scanning platform adapted to receive the package supplied by the transport module, a first scanner positioned at a first location with respect to the seal, and a second scanner positioned at a second location with respect to the seal. The second location can be opposite to the first location. The first scanner and second scanner can be separated by a gap distance. The first scanner can measure a first distance from the first scanner to the seal and the second scanner can measure a second distance from second scanner to the seal. The control unit can move the package to a first station if the difference between the gap distance and combined first distance and second distance equals the predetermined thickness of the integral seal. The control unit can move the package to a second station if the difference between the gap distance and combined first distance and second distance is greater than the predetermined thickness of the integral seal.

In another embodiment, the inspection station includes a first optical scanner positioned at a first location with respect to the seal, and a second optical scanner positioned at a second location with respect to the seal, the second location being opposite to the first location. The first optical scanner and second optical scanner can be separated by a gap distance. The first optical scanner includes a first emitter and a first sensor. The first emitter can emit a first beam and the first sensor can measure a first distance traveled by the first beam from the seal to the first sensor. The second optical scanner includes a second emitter and a second sensor. The second emitter can emit a second beam and the second sensor can measure a second distance traveled by the second beam from the seal to the second sensor. The control unit can move the package to a first station if the difference between the gap distance and combined first distance and second distance equals the predetermined thickness of the integral seal. The control unit can move the package to a second station if the difference between the gap distance and combined first distance and second distance is greater than the predetermined thickness of the integral seal.

Embodiments also include a method of inspecting the integrity of a seal. The method can include the steps of providing an inspection station according to any of the embodiments described herein, supplying a package to the scanning platform, measuring a first distance from the seal using the first scanner, measuring a second distance from the seal using the second scanner, moving the package to a first station if the difference between the gap distance and combined first distance and second distance equal the predetermined thickness of the integral seal, and moving the package to a second station if the difference between the gap distance and combined first distance and second distance is greater than the predetermined thickness of the integral seal.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
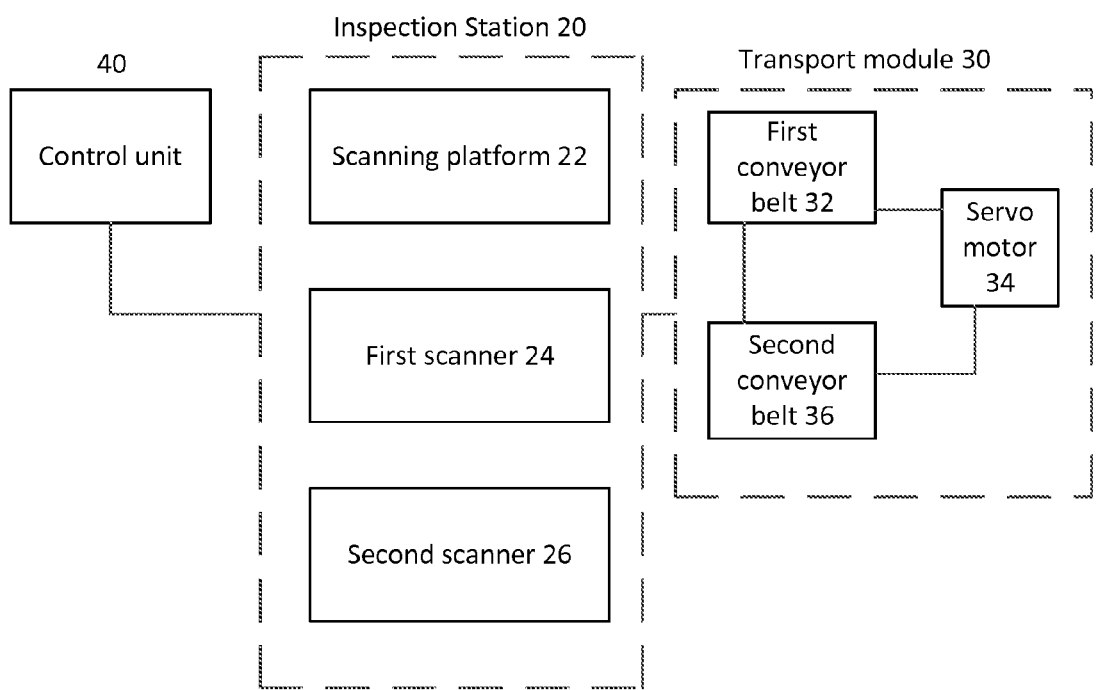
FIG. 1 is a schematic of a system for inspecting the integrity of a package with a seal according to some embodiments of the invention.

FIG. 1 shows a schematic of a system 10 for determining the integrity of a package 100 with a seal. The system 10 can be integrated into a production line of a food product. For example, the production line can involve one or more stations, such that the food package is properly dried, coated with preservatives, treated to ensure that moisture and oxygen levels are below predetermined thresholds, vacuum sealed, and inspected. In such an exemplary embodiment, the system 10 can be the last of the several stations. The system 10 can be useful for inspecting the integrity of sealed food packages. The system 10 can send packages with proper or integral seals to a shipping container or a storage facility. The system 10 can send packages with an improper seal (e.g.: package with trapped food product in the seal) to a different location (e.g.: a "reject station" or storage area for packages with damaged seals). Any of the well-known types of package can be used and specific types of the package or seal do not limit the scope or the applicability of embodiments of the invention. For example, the embodiments of the invention can be used with packaging for medical equipment such as scalpels, for example, where the sterility needs to be maintained.

With continued reference to FIG. 1, the system 10 includes an inspection station 20. The inspection station 20 can be operatively coupled to a transport module 30. The transport module 30 includes a first conveyor belt 32 for transporting the package 100 to a scanning platform 22. The transport module 30 can include a servomotor 34 to drive the first conveyor belt 32. In some embodiments, a stepper motor can be used instead of or in addition to the servomotor 34. The first conveyor belt 32 moves about at a speed of 50 inches per second. In some embodiments, the transport module 30 can centrally supply packages 100 to every station of a production line in food packaging plant.

Figure 2:
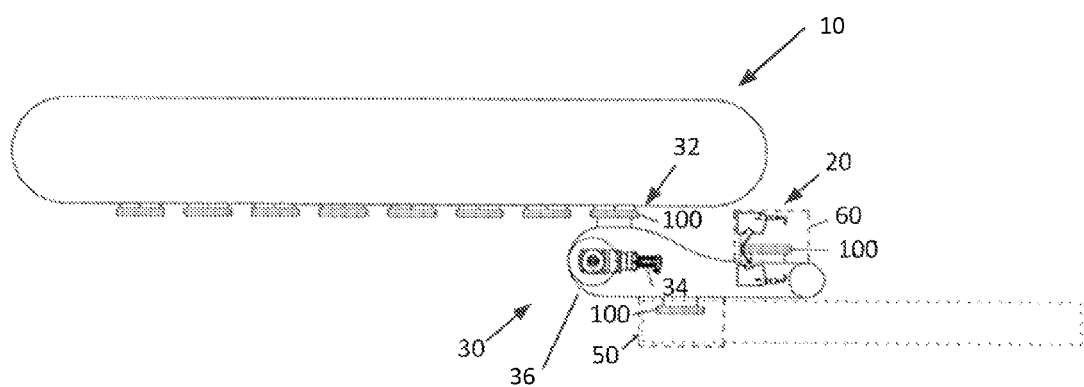
FIG. 2 is a process flow diagram of the system of FIG. 1.

As best seen in FIG. 2, the scanning platform 22 receives the package 100 supplied by the transport module 30. The package 100 is sealed prior to being positioned on the scanning platform for inspection. A proper or an integral seal should have a predetermined thickness x. The inspection station 20 includes a first scanner 24 positioned at a first location with respect to the seal, and a second scanner 26 positioned at a second location with respect to the seal. The second location can be opposite to the first location. In the illustrated embodiment, the first scanner 24 and second scanner 26 are separated by a gap distance y. The first and second scanner 26 can be useful for inspecting the integrity of the seal to determine if a food product is trapped in the seal.

With continued reference to FIG. 2, the first scanner 24 can be to measure a first distance y1 from the first scanner 24 to the seal S and the second scanner 26 can be adapted to measure a second distance y2 from second scanner 26 to the seal S. The first distance y1 can be equal to the second distance y2 when the difference between the gap distance y and the combined first and second distance y1, y2 equals the predetermined thickness x. In such an embodiment, the system 10 treats the seal as an integral or a proper seal. In other embodiments, the difference between the combined first and second distance y1, y2 and the gap distance y exceeds the predetermined thickness x. Food product trapped in the seal, non-uniform sealing, poor vacuum retention of the package 100 or similar reasons can lead to the seal thickness being larger than the predetermined thickness x. In such embodiments, the system 10 treats the seal as a non-integral seal. The difference between the gap distance y and the combined first and second distances can be between approximately 4 inches and approximately 0.0004 mils.

In some embodiments, the first and second distances y1, y2 can be measured over varying widths of the seal. The first and second distances y1, y2 can be measured non-sequentially over the width of the seal. The first and second distances can be measured simultaneously over the entire width of the seal. The first distance y1 and second distance y2 can be measured simultaneously over an area of the seal. The size of the seal that can be scanned can be adjusted by adding or subtracting lasers.

Referring back to FIG. 1, the system 10 includes a control unit 40 operatively coupled to the inspection station 20. The inspection system 10 transmits the measured first and second distances y1, y2 to the control unit 40. The control unit 40 uses the measured first and second distances y1, y2 to move the package 100 to one of a first station 50 or a second station 60. The control unit 40 is adapted to move the package 100 to the first station 50 if the difference between the gap distance y and combined first distance y1 and second distance y2 equals the predetermined thickness x of the integral seal. The control unit 40 is adapted to move the package 100 to the second station 60 if the difference between the gap distance y and combined first distance y1 and second distance y2 is greater than the predetermined thickness x of the integral seal.

Figure 3:
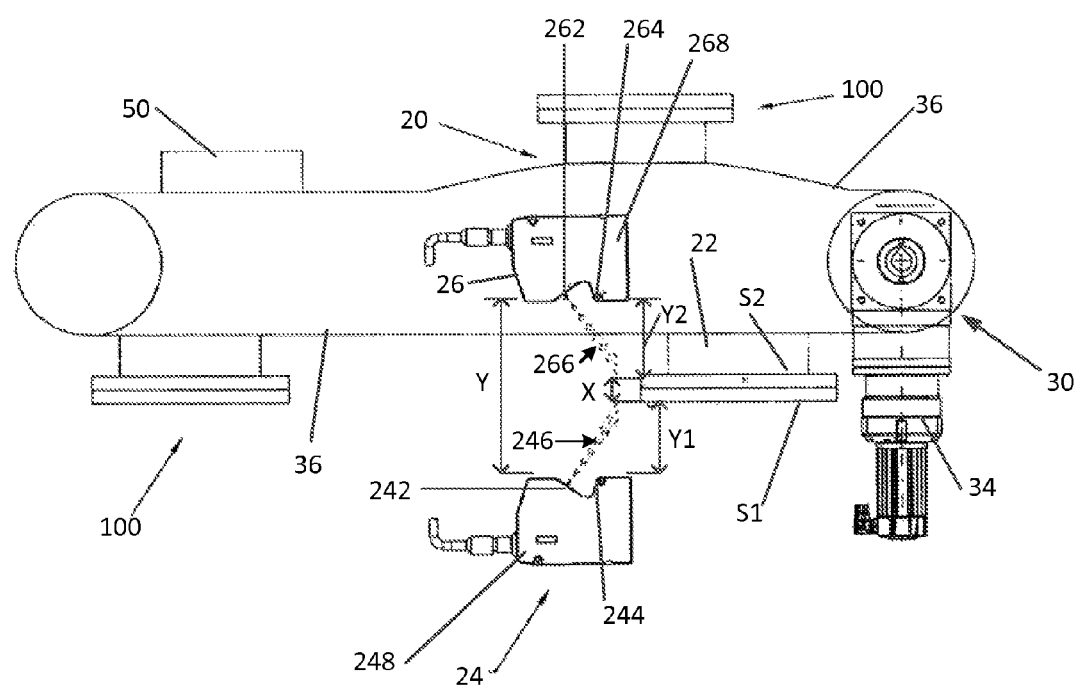
FIG. 3 is a process flow diagram of the system of FIG. 1 with a detailed view of the inspection station.

As best seen in FIGS. 2 and 3, the transport module 30 can include a second conveyor belt 36 for transporting the package 100 to one of the first and second stations 50, 60. The servomotor 34 can drive the second conveyor belt 36. The second conveyor belt 36 can be coupled to the control unit 40, such that when the control unit 40 uses the first and second distances y1, y2 to decide if the seal is integral, the control unit 40 engages the second conveyor belt 36 to move the package 100 to the first station 50 if the seal is integral, or to the second station 60 if the seal is non-integral. The first station 50 and second station 60 can be referred to as "accept station" and "reject station" respectively, or "go station" and "no-go station" respectively. In the embodiment illustrated in FIG. 2, the second station 60 is positioned adjacent the scanning platform, so that if the seal is improper, the package can be dropped from the production line. In other embodiments, packages with improper seal can be moved to a location away from the production line.

In some embodiments, the first and second scanners 24, 26 can be optical scanners. The first scanner 24 can include a first emitter 242 and a first sensor 244, and the second scanner 26 can include a second emitter 262 and a second scanner 26. The first and second emitters 242, 262 can emit a first beam 246 and a second beam 266, respectively. The first and second beams 246, 266 can encounter reflection at a first surface "S1" and a second surface "S2" of the seal, respectively. The first and second sensors 244, 264 can measure the distance traveled by the first and second beams 246, 266 after reflection from the first and second surfaces Si and S2. In some embodiments, the first and second emitters 242, 262 can emit laser beams. In other embodiments, the first and second emitters 242, 262 can emit electromagnetic radiation such as ultraviolet, visible light, infrared, X-ray, microwave, radio frequency radiation and the like. The wavelength of radiation emitted by the first and second emitters 242, 262 does not limit the scope or applicability of embodiments of the invention, and any source of electromagnetic radiation is contemplated.

In some embodiments, the first and second sensors 244, 264 can be optical sensors including one or more pixel sensors, photodetectors or amplifiers to measure the distance between the first and second sensors 244, 264 and the first and second surfaces of the seal S1, S2, respectively. Optical sensors such as complementary metal oxide semiconductors (CMOS), charge coupled device (CCD), infrared proximity sensors, thermal imaging sensors and the like can be used without loss of functionality. The sampling time of the first and second optical sensors can be approximately between about 16 msec and 32 msec. The first and second sensors 244, 264 can measure scattered radiation from the surface of the seal and minimize background radiation from areas other than the first and second surface of the seal. The first and second sensors 244, 264 can include one or more polarizers to minimize errors in measurement due to the reflected first and second beams being polarized differently from one another. The first and second sensors 244, 264 can include a high dynamic range such that distance measurement of first and second distances y1, y2 can be performed from substantially black (or radiation-absorbing) first and second surfaces S1, S2 of the seal, as well substantially white (or radiation-reflecting) first and second surfaces S1, S2 of the seal. Such embodiments can be useful for inspecting packages of various colors and surface reflectivity or transparent packages and/or seals.

In some embodiments, the first emitter 242 and first sensor 244 can be integrally housed inside the first scanner 24 and the second emitter 262 and second sensor 264 can be integrally housed inside the second scanner 26. In such embodiments, a first housing 248 of the first scanner 24 includes the first emitter 242 and first sensor 244 and a second housing 268 of the second scanner 26 includes the second emitter 262 and the second sensor 264. The first and second housing 248, 268 can each have an aperture (not shown) for emission and sensing of radiation. The first and second housing 248, 268 can be of durable rugged construction (e.g.: aluminum) and be hermetically sealed to secure the emitters, sensors and other components from damage.

In some embodiments, the control unit 40 can be integrally housed in the first and second scanners, 24, 26. In other embodiments, the control unit 40 can be a computer (e.g.: desktop, laptop computer or similar devices, not shown) operatively coupled to the inspection station 20 and the transport module 30. The control unit 40 can issue commands that (i) communicate with the transport module 30 to move the package 100 to the scanning platform, (ii) allow a user to input measurement settings such as package size, type, inspection time, etc. (iii) communicate with the first and second scanners 24, 26 to measure first and second distances y1, y2, (iv) receive the measured first and second distances y1, y2 from the first and second scanners 24, 26, and (v) communicate with the transport module 30 to move the package 100 to the first station 50 or the second station 60.

Figure 4:
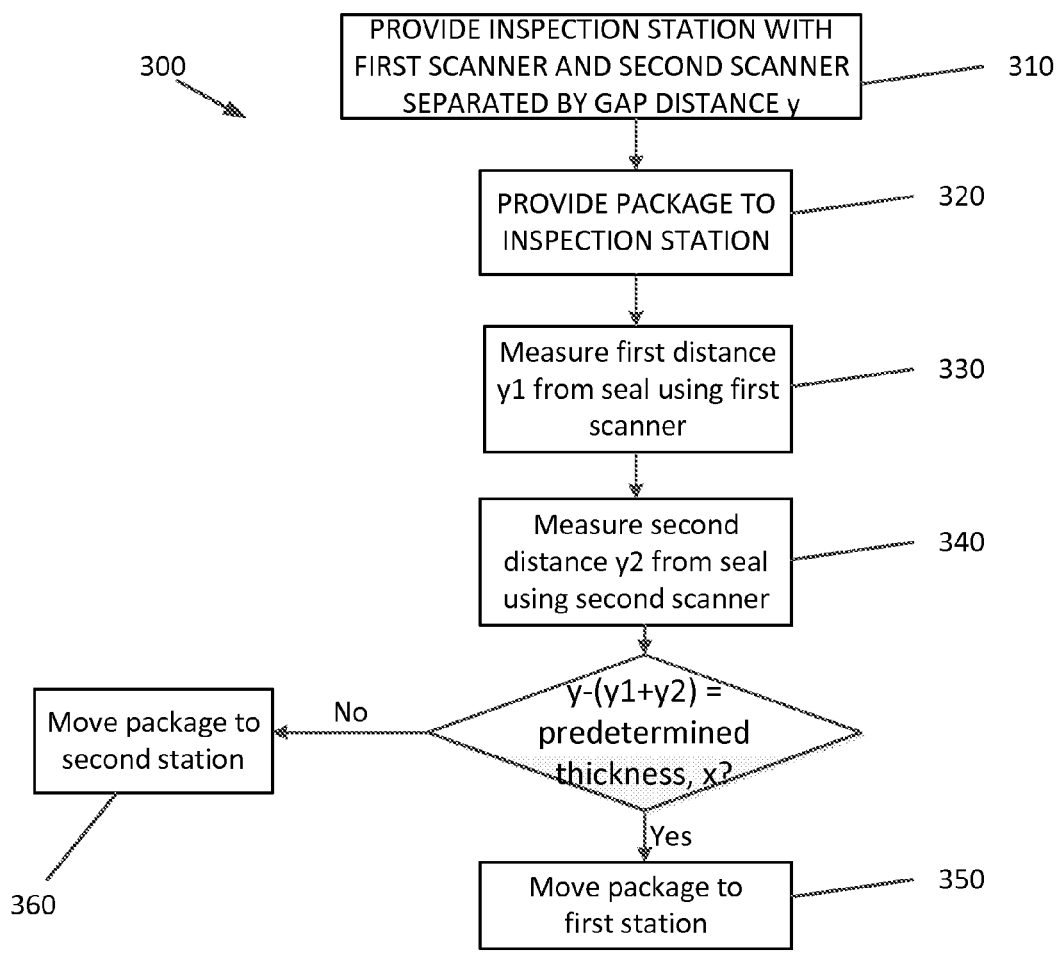
FIG. 4 is a flow chart of a method for inspecting the integrity of a package with a seal according to some embodiments of the invention.

A method 300 of inspecting the integrity of a seal of a package can include one or more of the following steps, as shown in FIG. 4: providing an inspection station according to any of the embodiments described elsewhere herein (310); supplying a package to the scanning platform (320); measuring a first distance y1 from the seal using the first scanner (330); measuring a second distance y2 from the seal using the second scanner (340); moving the package 100 to a first station if the difference between the gap distance y and combined first distance y1 and second distance y2 equal the predetermined thickness x of the integral seal (350); and moving the package to a second station if the difference between the gap distance y and combined first distance y1 and second distance y2 is greater than the predetermined thickness x of the integral seal (360).

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

What is claimed is:

1. A system for determining integrity of a package with a seal, wherein an integral seal has a predetermined thickness, the system comprising:
   an inspection station operatively coupled to a transport module, the inspection station comprising
      a scanning platform adapted to receive the package supplied by the transport module,
      a first scanner positioned at a first location with respect to the seal, and
      a second scanner positioned at a second location with respect to the seal, the second location being opposite to the first location, the first scanner and second scanner separated by a gap distance; and
   a control unit operatively coupled to the inspection station, wherein
   the first scanner is adapted to measure a first distance from the first scanner to the seal and the second scanner is adapted to measure a second distance from second scanner to the seal,
   the control unit is adapted to move the package to a first station if the difference between the gap distance and combined first distance and second distance equals the predetermined thickness of the integral seal, and
   the control unit is adapted to move the package to a second station if the difference between the gap distance and combined first distance and second distance is greater than the predetermined thickness of the integral seal.

2. The system of claim 1, wherein the transport module includes a first conveyor belt for transporting the package to the scanning platform and a second conveyor belt for transporting the package to one of the first and second stations.

3. The system of claim 2, wherein the transport module includes a servomotor, the servomotor adapted to drive the first conveyor belt and the second conveyor belt.

4. The system of claim 2, wherein the first conveyor belt moves at a speed of about 50 inches per second.

5. The system of claim 1, wherein the difference between the gap distance and the combined first and second distances is between approximately 0.0004 mls and approximately 4 inches.

6. The system of claim 1, wherein the first distance is equal to the second distance when the difference between the gap distance and the combined first and second distance equals the predetermined thickness.

7. The system of claim 1, wherein the inspection system transmits the measured first and second distances to the control unit, and the control unit uses the measured first and second distances to move the package to one of the first station or the second station.

8. An inspection system for determining the integrity of a seal of a package, the inspection system comprising:
   an inspection station operatively coupled to a transport module, the inspection station comprising
      a scanning platform adapted to receive the package supplied by the transport module,
      a first optical scanner positioned at a first location with respect to the seal, and
      a second optical scanner positioned at a second location with respect to the seal, the second location being opposite to the first location, the first scanner and second optical scanners separated by a gap distance; and
   a control unit operatively coupled to the inspection station, wherein
   the first optical scanner includes a first emitter and a first sensor, the first emitter adapted to emit a first beam and the first sensor adapted to measure a first distance traveled by the first beam from the seal to the first sensor, the second optical scanner includes a second emitter and a second sensor, the second emitter adapted to emit a second beam and the second sensor adapted to measure a second distance traveled by the second beam from the seal to the second sensor, the control unit is adapted to move the package to a first station if the difference between the gap distance and combined first distance and second distance equals the predetermined thickness of the integral seal, and the control unit is adapted to move the package to a second station if the difference between the gap distance and combined first distance and second distance is greater than the predetermined thickness of the integral seal.

9. The inspection system of claim 8, wherein the first sensor measures the first distance from a first surface of the seal to the first sensor and the second sensor measures the second distances from a second surface of the seal to the second sensor.

10. The inspection system of claim 9, wherein the first beam is reflected by the first surface of the seal and the second beam is reflected by the second surface of the seal.

11. The inspection system of claim 10, wherein the first distance and second distance are distance traveled by reflected beams from the seal.

12. The inspection system of claim 8, wherein the first and second sensors are CMOS imaging sensors.

13. The inspection system of claim 8, wherein the sampling time of the first and second optical sensors range from about 16 msec to about 32 msec.

14. The inspection system of claim 8, wherein the first emitter and first sensor are integrally housed inside the first optical scanner and the second emitter and second sensor are integrally housed inside the second optical scanner.

15. The inspection system of claim 8, wherein the first beam and second beam are laser beams emitted by the first emitter and the second emitter.

16. A method of inspecting the integrity of a seal of a package, the method comprising:
    providing an inspection station comprising
        a scanning platform,
        a first scanner positioned at a first location with respect to the seal, and
        a second scanner positioned at a second location with respect to the seal, the second location opposite the first location, the first scanner and second scanner separated by a gap distance;
    supplying a package to the scanning platform;
    measuring a first distance from the seal using the first scanner;
    measuring a second distance from the seal using the second scanner;
    moving the package to a first station if the difference between the gap distance and combined first distance and second distance equal the predetermined thickness of the integral seal; and
    moving the package to a second station if the difference between the gap distance and combined first distance and second distance is greater than the predetermined thickness of the integral seal.

17. The method of claim 16, wherein the first and second distances are each measured over a width of the seal.

18. The method of claim 17, wherein the first and second distances are each measured non-sequentially over the width of the seal.

19. The method of claim 18, wherein the first and second distances are each measured simultaneously over the width of the entire seal.

20. The method of claim 16, further comprising measuring the first distance and second distance simultaneously over an area of the seal.

* * * * *